United States Patent [19]

Wool

[11] Patent Number: 4,979,312

[45] Date of Patent: Dec. 25, 1990

[54] ARCH WIRE TORQUE MEASURING DEVICE

[76] Inventor: Arthur L. Wool, Faust Rd., Box 210J, Sinking Spring, Pa. 19608

[21] Appl. No.: 378,040

[22] Filed: Jul. 11, 1989

[51] Int. Cl.⁵ .......................... A61C 19/04; G01B 3/18
[52] U.S. Cl. ........................................ 33/513; 33/813; 33/818; 433/72
[58] Field of Search ................. 33/513, 514, 813, 818, 33/828, 830; 433/72, 75, 3

[56] References Cited

U.S. PATENT DOCUMENTS

| | | | |
|---|---|---|---|
| 997,989 | 7/1911 | Glickert | 33/813 |
| 1,082,052 | 12/1913 | Strang | 433/20 |
| 4,184,259 | 1/1980 | Sosnay | 433/4 |

FOREIGN PATENT DOCUMENTS

| | | | |
|---|---|---|---|
| 0240330 | 11/1911 | Fed. Rep. of Germany | 33/828 |
| 0131568 | 8/1919 | United Kingdom | 33/813 |

Primary Examiner—William A. Cuchlinski, Jr.
Assistant Examiner—Alvin Wirthlin
Attorney, Agent, or Firm—Antonelli, Terry, Stout & Kraus

[57] ABSTRACT

A method and device for measuring torque in a rectangular or square orthodontic arch wire wherein the orthodontic arch wire is held relative to the torque indicator scale in such a manner that the presence and amount of torque in the orthodontic arch wire can be determined directly from the torque indicator scale.

23 Claims, 2 Drawing Sheets

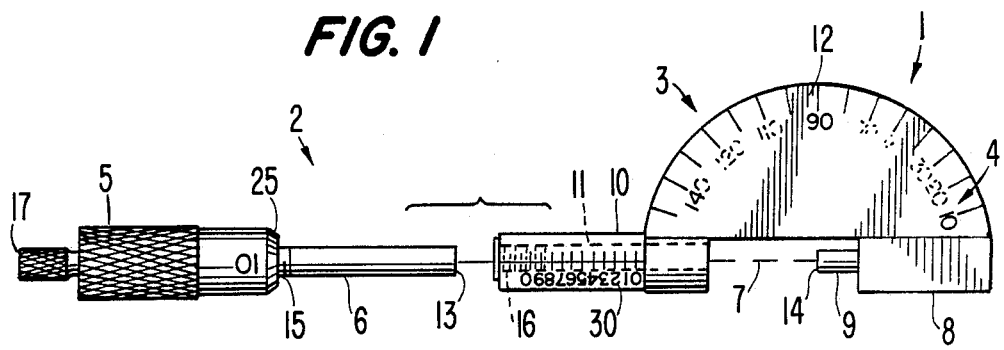
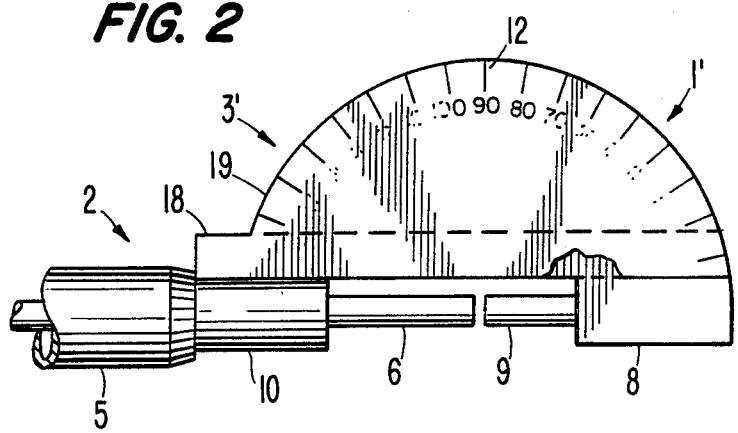
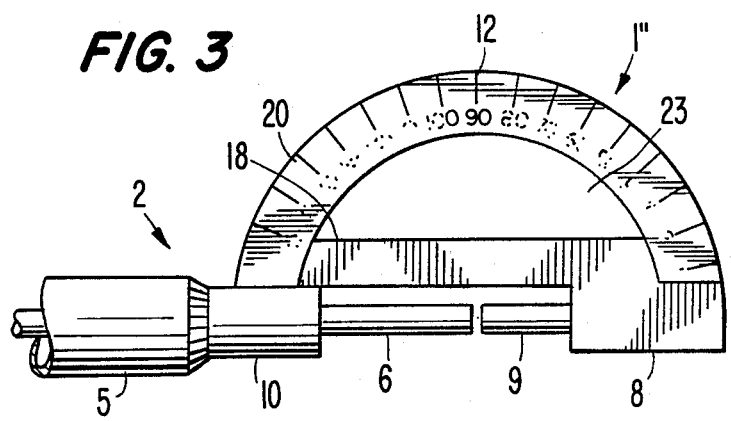

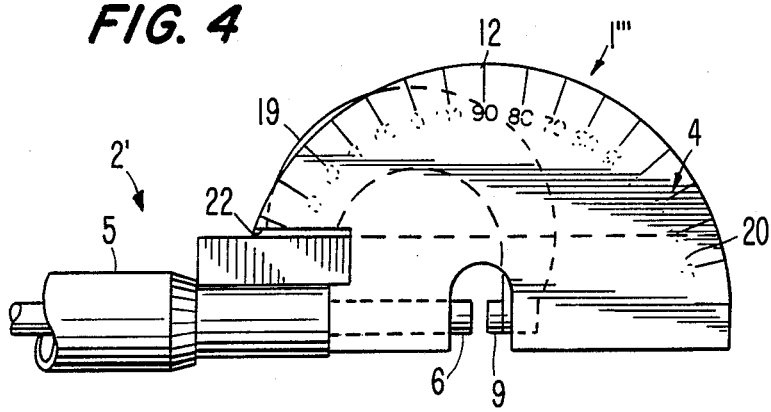
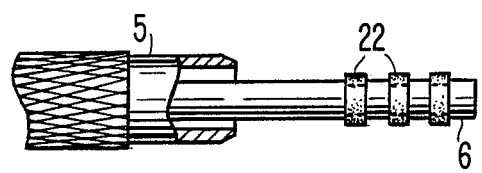
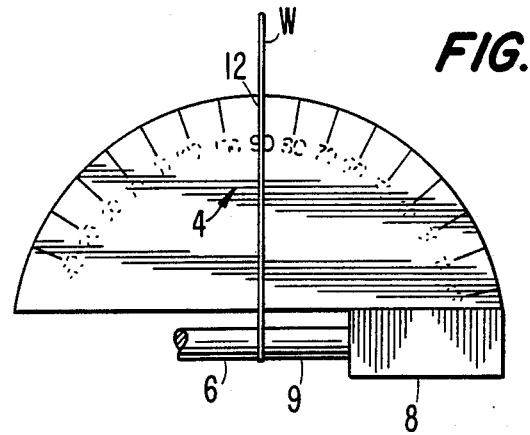
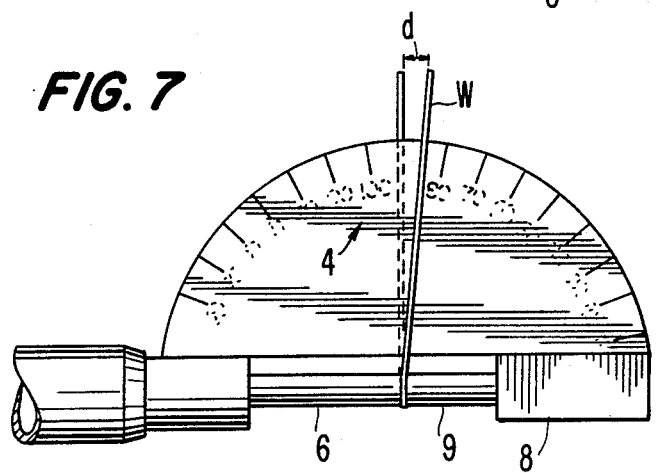

4,979,312

ARCH WIRE TORQUE MEASURING DEVICE

BACKGROUND OF THE INVENTION

The present invention relates to a measuring device and measuring method and, more particularly, to a measuring device and method for measuring a torque in rectangular or square preformed orthodontic arch wires.

Arch wires of the aforementioned type disclosed in, for example, U.S. Pat. No. 4,424,033 are used in conjunction with tooth brackets for correction of all classes of malocclusions using edgewise or like wire techniques. In corrections using arch wires, the brackets are secured to the teeth of the patient by the use of bands to which the brackets are welded or by cementing brackets directly to the teeth. Generally, in each number of stages during the course of the treatment, an arch wire is secured to the brackets. As the treatment progresses, the arch wire which is used more or less closely approaches the ideal arch form thereby progressively correcting misalignments of the teeth of the patient.

Arch wires for orthodontic appliances may be formed from straight wire blanks by techniques such as disclosed in, for example, U.S. Pat. No. 4,566,305 wherein the wire blanks are formed into arches by way of a swing-arm bender.

One problem with arch wires resides in the fact that when the wires are formed, the wires may have a certain internal torque therein resulting from, for example, the forming of the arch wire. The existence of such torque creates difficulties when the arch wires are used with so-called pre-torqued wire brackets which generally have a slot for accommodating the arch wires, with the brackets having a preset predetermined torque.

If an arch wire has no internal torque no difficulties are created since the orthodontist will know the preset degree of torque in the bracket and can reasonably assume that a certain amount of torque will be placed on the tooth being corrected. However, if due to, for example, forming of the arched wires, shipping, or subsequent handling or the like, the arch wire develops an internal torque, and such torque will either increase or decrease the amount of torque set by the pre-torque tooth bracket depending upon which way the arch wire is inserted into the bracket.

Conventionally, orthodontist have used a very simple test to determine whether an arch wire has a torque. More particularly, the arch wire is simply placed on a flat plate glass, pressed at the center of the arch, and then turned over and the same operation is carried out. If a torque exists in the arch wire, the legs of the arch will move upward in one of the two positions being tested, since, in the other of the two positions, the legs will be forced down by the torque in the arch wire into the glass.

While the above conventional technique does easily ascertain whether a torque exists, such technique does not provide any accurate measurement of just how much torque exists in the arch wire.

Another technique has been proposed utilizing two pair of orthodontic pliers, with one pair of the pliers being placed adjacent to a leg of the arch wire while the other pair of pliers is placed at the other leg. The orthodontic pliers open and close alternately and at a 180° out of phase with one another. Consequently, as one of the pair of pliers is closing on one leg of the wire, the other pair of pliers will be opening. If a torque exist in the wire, the leg adjacent to the pair of pliers which is opening will move the opened jaws.

While this last proposed technique also provides a simple test for determining the existence of the torque, it does not provide any degree of measurement for just how much torque exist in the arch wire.

SUMMARY OF THE INVENTION

The aim underlying the present invention essentially resides in providing a measuring device for measuring a torque in rectangular or square preformed orthodontic arch wires which provides an accurate measurement of the exact amount of torque which does exist in the arch wire thereby providing the orthodontist with valuable information to assist in determining how to use the arch wire in conjunction with existing pretorqued tooth brackets.

In accordance with advantageous features of the present invention, a measuring device for measuring torque in orthodontic arch wires is provided which includes a handle or grip portion having a torque measuring gauge mounted on a support portion fixed to the handle or grip portion. The handle or grip portion includes a first barrel or cylindrical member, with a second barrel or cylindrical member being provided and being adapted to be coaxially mounted on the first barrel or cylindrical member so as to be movable relative thereto. The first barrel or cylindrical member includes a rod or stem portion coaxially with and extending along a longitudinal axis thereof. The outer stem portion terminates at a free end thereof and a substantially flat surface cooperable with a fixed substantially flat surface mounted on the support portion at a position opposite the free end of the rod or stem portion.

The rod or stem portion may, according to the present invention, be accommodated in the second barrel or cylindrical member with a friction fit or the internal portion of the second barrel or cylindrical member or external surface of the rod or stem portion may be provided with means for enabling a frictional engagement between the rod or stem portion and internal surface of the second barrel or cylindrical member so as to permit the barrel or cylindrical members to be displaced relative to each other while preventing an accidental or unintentional separation of the two members when the measuring device is not in use.

Preferably, according to the present invention, to provide a more positive displacement of the barrel or cylindrical members relative to each other, the bore in the second barrel or cylindrical member accommodating the rod or stem portion includes an internal threaded portion along at least an axial extent thereof, with the rod or stem portion being provided with a corresponding external threaded portion cooperable with the internal threaded portion.

To enable, for example, a measuring of the exact thickness of the arch wire being used, an external surface of the second barrel or cylindrical member may be provided with a longitudinally extending scale over a portion thereof cooperable with a forward edge of the first barrel or cylindrical member also provided with a scale, with the two scales being used and readable in a manner of a conventional micrometer.

In accordance with still further features of the present invention, the support portion fixed to the grip or handle portion need not have any specific configuration, with the only requirement of a support portion being that the fixed substantially flat surface is mounted so as to be in direct opposition to the substantially flat surface portion of the free and of the displaceable rod or stem portion of the second barrel or cylindrical member thereby enabling a gripping of the arch wire between the substantially flat portions, and a center or zero of the torque scale extends through a line passing through a line created by a contact between the substantially flat surface of the free end of the rod or stem portion and the fixed substantially flat surface.

The torque measuring scale may, in accordance with the present invention be printed or inscribed directly on the support portion or a separate member may be provided and mounted on the support portion in such a fashion that the center or zero line passes through the line created by the contacting of the two substantially flat surfaces.

The torque measuring scale of the present invention is provided with indicia enabling an exact and accurate measuring of both positive and negative torque at any point along the arch wire.

It is also possible in accordance with the present invention to provide an accessory for mounting the item to be measured relative to the torque indicator scale. For this purpose a substantially U-shaped member may be provided having an adjustable member such as, for example, a threaded screw or spindle member, disposed in one leg of the U-shaped member, with the adjustable member having a substantially flat free end portion adapted to contact the item to be measured so as to grip or hold the member between the free end of the adjustable member and the other leg of the U-shaped member. The other leg of the U-shaped member is provided with an extension in the form of, for example, a pointer or the like which is adapted to cooperate with the measuring scale when the accessory is mounted in the support system which the measuring gauge is mounted. By virtue of the arrangement it is possible to accurately measure a torque or deflection of an item having a relatively short axial length and which has a substantially linear rather than arched configuration.

In accordance with advantageous features of the measuring method of the present invention, a torque indicator scale means is provided having a zero torque indexing point, and the arch wire is held along two opposed parallel surfaces thereof in a position relative to the torque indicator scale means in such a manner that a line passing through the zero index point extends perpendicular to a midpoint of a surface of the arch wire connecting the two opposed parallel surfaces and with the arch wire extending on both sides of the torque indicator scale means, with a deviation of the arch wire from the zero index point on the torque indicated scale means being read to provide the value and direction of the torque.

Accordingly, it is an object of the present invention to provide a measuring device for measuring a torque in rectangular or square preformed orthodontic arch wires which avoids, by simple means, shortcomings and disadvantages encountered in the prior art.

Another object of the present invention resides in providing a measuring device for measuring torque in rectangular or square preformed orthodontic arch wires which enables not only a determination of the existence of a torque in the arch wires but also a measurement of the torque, both positive and negative, at any point along the arch wire.

A still further object of the present invention resides in providing a measuring device for measuring a torque in rectangular or square preformed orthodontic arch wires which is simple in construction and therefore relatively inexpensive to manufacture.

The above and other objects, features, and advantages of the present invention will become more apparent from the following description when taken in connection with the accompanying drawings which show, for the purposes of illustration only, several embodiments in accordance with the present invention.

BRIEF DESCRIPTION OF THE DRAWINGS

FIG. 1 is a exploded view of a measuring device for measuring torque in an orthodontic arch wire constructed in accordance with one embodiment of the present invention;

FIG. 2 is a side view of another embodiment of a measuring device for measuring torque in an orthodontic arch wire constructed in accordance with another embodiment of the present invention;

FIG. 3 is a side view of a further embodiment of a measuring device for measuring torque in an orthodontic arch wire constructed in accordance with the present invention;

FIG. 4 is a side view of yet another embodiment of a measuring device for measuring torque in an orthodontic arch wire constructed in accordance with the present invention;

FIG. 5 is a side view of a portion of the measuring device for measuring torque in an orthodontic arch wire constructed in accordance with the present invention;

FIG. 6 is a partial schematic view of the measuring device of the present invention with an arch wire mounted therein, which arch wire registers no torque; and FIG. 7 is a partial schematic view of the measuring device of the present invention with an arch wire mounted therein, which arch wire has a torque therein.

DETAILED DESCRIPTION

Referring now to the drawings wherein like reference numerals are used throughout the various views to designate like parts, and, more particularly, to FIG. 1, according to this figure, a measuring device generally designated by the reference numeral 1 for measuring torque in orthodontic arch wires includes a handle portion generally designated by the reference numeral 2, a support portion generally designated by the reference numeral 3, and an arcuate torque indicator scale generally designated by the reference numeral 4, with the handle portion including a first barrel or cylindrical member 5 having a stem or rod 6 fixed thereto and extending along a longitudinal center axis 7 of the barrel or cylindrical member 5. The handle portion 2 includes a second barrel or cylindrical member 10 disposed coaxially with respect to the first barrel or cylindrical member 5, with the second barrel or cylindrical member 10 including a bore 11 extending therethrough for accommodating the rod or stem 6.

The support portion 3 has a substantially arcuate configuration and terminates in an end of portion 8 having fixed thereto a rod or stem 9, with the rod or stem 9 being disposed along the longitudinal center axis 7. A free end of the rod or stem 6 is provided with a substantially flat surface 13 which is adapted to cooperate with a corresponding substantially flat surface 14 provided on a free end of the stem or rod 9.

The stem or rod 6 includes a threaded portion 16 along at least a portion of an outer circumferential surface thereof, with the threaded portion 15 being adapted to threadably engage a corresponding threaded portion 16 provided along at least an axial length of the bore 11 of the second barrel or cylindrical member 10. Upon a rotation of the first barrel or cylindrical member 5 relative to the second barrel or cylindrical member 10, the threaded portions 15, 16 interengage and the stem or rod 6 is displaced toward or away from the fixed stem or rod 9.

The torque indicator scale 4 includes suitable indicia for providing a visual indication of the torque, with a zero index point 12 of the torque indicator scale 4 being disposed on the torque indicator scale 4 in such a manner that a line passing through the zero index point 12 extends through a line formed when the two substantially flat surfaces 13, 14 are in contact. The torque indicator scale 4 may extend along the entire arc of the support portion 3; however, as a practical matter, indicia in a range of, for example, 15° on each side of the zero point 12 is generally sufficient since any measurements outside such range would render the orthodontic arch wire unsuitable for practical use.

As shown in FIG. 2, a measuring device generally designated by the reference numeral 1' includes a support portion generally designated by the reference numeral 3' formed as an axially extending bar member 18 fixedly connected to the barrel or cylindrical member 10, with the bar member 18 terminating in the end portion 8 having fixed thereto the rod or stem 9. An arcuate scale plate member 19 is mounted to the bar portion 18 in such a manner that the zero index point 12 of the torque indicator scale 4 is disposed along a line extending through the zero index point 12 and a line formed by the contact between the two substantially flat surfaces 13, 14 of the rods or stems 6, 9. In all other respects the embodiment of FIG. 2 corresponds to the embodiment of FIG. 1.

In the embodiment of FIG. 3, in order to facilitate a visual alignment of the respective ends of the arch wire on the respective sides of the torque indicator scale 4, rather than provide a solid scale plate member 18 as shown in FIGS. 1 and 2, a measuring device generally by the reference numeral 1'' including a handle portion generally designated by the reference numeral 2'; may include a sector shaped-plate 20 mounted on the bar portion 18, with the sector shaped-plate 20 having an opening 23 therein. The sector-shaped plate 20 is mounted in such a manner that the zero index point 12 is disposed relative to the stem or rods 6, 9 in the same manner as described hereinabove. However, it is also possible in accordance with the present invention to provide a transparent member having the torque indicator scale 4 embossed, imprinted, inscribed or otherwise affixed thereto.

In FIG. 4, a measuring device generally designated by the reference numeral 1''' includes a support portion which is formed by an arched portion 19 of a conventional micrometer generally designated by the reference numeral 2', with the torque measuring scale 4 being formed by a conventional protractor 20 mounted on the arched portion 19 in such a fashion that the 90° index mark normally found on a conventional protractor 20 is disposed relative to the rod or stem portion 6, 9 in the same manner as the zero index point 12 in the above-described embodiments. As shown in FIG. 4, to enable a mounting of the conventional protractor 20 to the conventional micrometer 2', it is only necessary to provide a notch 22 at one end thereof to enable an alignment of the 90° index mark relative to the closed beaks of the micrometer 2'.

While the above-described embodiments employ a threaded connection 15, 16 between the first and second barrel or cylindrical members 5, 10, it is also possible in accordance with the present invention to provide for a frictional engagement between the first and second barrel members 5, 10. The frictional engagement could be obtained by providing for a friction fit between the rod or stem portion 6 and the internal surface of the bore 11 of the second barrel or cylindrical member 10; however, such approach would increase the overall manufacturing cost due to required tolerances. Consequently, as shown in FIG. 5, a plurality of, for example, O-rings 22 may be disposed in spaced grooves or the like provided in the outer peripheral surface of the stem or rod 6, with the O-rings cooperating with the internal surface of the bore 11 of the second barrel or cylindrical member 10.

By providing suitable scales 25, 30 FIG. 1 on the respective barrel or cylindrical members 5, 10, it is possible for the orthodontist to also measure the exact thickness of the orthodontic arch wire being used.

A grip means 17 is provided at a free end of the barrel or cylindrical member 5 so as to facilitate an operation of the measuring device and fine adjustment of the releasable holding means. The grip means 17 may include a conventional rachet or pawl mechanism which provides a tactile or audible indication of a sufficient clamping of the arch wire W between the stems or rods 6,9.

In operation, as shown in FIGS. 6 and 7, an arch wire W is placed between the substantially flat surfaces 13, 14 of the rods or stems 6, 9 of the measuring device as 1, 1', 1'' or 1''', with the arch wire W being held relative to the torque indicator scale 4. If no torque exist in the arch wire W, the two ends of the arch wire W will be in alignment with the zero indexing point 12 of the torque indicator scale 4 or 90° index mark of the scale in FIG. 4, as shown most clearly in FIG. 6; however, if a torque exist in the arch wire W, the ends of the arch wire W are spaced from each other by an angular distance d as shown in FIG. 7 which distance can be directly read from the torque indicator scale 4. While FIG. 7 shows a plus torque indication, it is understood that a deflection to the left of FIG. 7 would indicate a minus torque.

Armed with the information of the presence and exact amount of the torque in the arch wire W, an orthodontist is then able to determine how to use the arch wire W in conjunction with existing pre-torqued brackets and can take the necessary compensatory measures.

In each of the above-described embodiments, the diametrical line of the arcuate torque indicator scale 4 in coincidental with the longitudinal center axis 7 of the rods or stems 6,9, with the arcuate torque indicator scale being supported such that a line passing through the zero index point 12 intersects the diametrical line of the arcuate torque indicator scale 4 at a right angle. Additionally, when measuring a torque in an arch wire W, in order to provide an arcuate measurement of the torque in the arch wire W, it is important that the arch wire W be held such that the line passing through the zero index point 12 extends substantially through a vertically extending mid-plane of the arch wire W and the diametrical line of the arcuate torque indicating scale 4 extends substantially through a horizontally extending mid-plane of the arch wire W such that the diametrical line and line extending through the index point 12 intersect substantially at a center point of the arch wire W.

It is also possible in accordance with the present invention to use, for example, a toggle switch mechanism for releasably gripping the arch wire W, or a conventional C-clamp arrangement, or any other means for releasably gripping and holding arch wire W relative to the torque indicator scale 4, with the only requirement being that the above-described relationship between the arch wire W and the torque indicator scale 4 be maintained when making the necessary torque measurements.

Additionally, in order to obtain a measurement of a torque or deflection of a substantially linear item of a relatively short length, it is also possible in accordance with the present invention to provide an accessory or auxiliary mounting member for the item to be measured in the form of a substantially U-shaped member (not shown) having an adjustable member (not shown) in one leg of the U-shaped member adapted to clamp the item to be measured between a free end of the adjustable member and the other leg of the U-shaped member. The other leg of the U-shaped member includes an extension (not shown) in the form of a pointer or the like which is adapted to cooperate with the torque indicator scale 4 when the accessory or auxiliary mounting member is clamped or held between the free ends of the rods or stem 6,9 to ensure an accurate measurement, the only requirement in that the extension member, when the accessing or auxiliary mounting member is mounted between the stems or rods 6,9 is in alignment with the zero index point 12 when the measuring device is in a zero or no torque condition.

While I have shown and described several embodiments in accordance with the present invention, it is understood that the same is not limited thereto but is susceptible to numerous changes and modifications as known to one or ordinary skill in the art, and I do not wish to be limited to the details shown and described herein but intend to cover all such modification as are encompassed by the scope of the appended claims.

I claim:

1. A measuring device for measuring a torque in an rectangular orthodontic arch wire, the measuring device comprising mounting means for mounting a torque indicator scale means thereon including a support means for supporting the torque indicator scale means and a handle means connected to said support means; and releasable holding means fixed to said mounting means for releasably holding the orthodontic arch wire relative to the torque indicator scale means for enabling a reading of the torque present in the orthodontic arch wire from the torque indicator scale means; and wherein said handle means includes means connected to said releasable holding means for enabling an axial displacement of said releasable holding means relative to said support means.

2. A measuring device according to claim 1, wherein said releasable holding means includes a first rod means having a substantially flat surface portion fixedly mounted to said support means, and a second rod means having a substantially flat surface portion, said second rod means being disposed opposite to said first rod means and along a common longitudinal axis, and wherein said second rod means is connected to said means for enabling a displacement of said releasable holding means whereby said second rod means is selectively moved toward and away from said first rod means.

3. A measuring device according to claim 2, wherein said handle means further includes a first barrel member fixedly connected to said support means, and wherein said means for enabling a displacement of said releasable holding means includes a second barrel member coaxially mounted on said first barrel member so as to be axially and rotatably displaceable relative thereto.

4. A measuring device according to one of claims 2 or 3, wherein said support means includes an arcuate support surface fixed to said first barrel member, and wherein said torque indicator scale means is provided along at least a portion of an outer periphery of said arcuate support surface, said torque indicator scale means including a plurality of torque-related indicia and a zero point index disposed on said torque indicator scale means in such a manner that a line passing through the zero point index extends through a line created by a contact between said substantially flat surface portion of said first and second rod means.

5. A measuring device according to claim 4, wherein said second rod means is mounted in said first barrel member with a frictional fit.

6. A measuring device according to claim 4, wherein means are provided on one of said second rod means or said first barrel member for providing frictional contact between said first barrel member and said second rod means.

7. A measuring device according to claim 4, wherein said second rod means is provided with an external threaded portion along at least a portion of an axial length thereof, and wherein said first barrel member includes an internal threaded portion along at least a portion of an axial length thereof engageable with the external threaded portion of said second rod means to permit an adjustable displacement of said second rod means relative to said first rod means.

8. A measuring device according to claim 7, wherein a grip means is provided at a free end of said second barrel member for facilitating an operation of said second barrel member and permitting a fine adjustment of said releasable holding means.

9. A measuring device according to claim 8, wherein scale means are provided on said first and second barrel member for enabling a measuring of a thickness of the rectangular orthodontic arch wire.

10. A device according to one of claims 2 or 3, wherein said support means includes a substantially flat axially extending bar member fixed to said first barrel member, said torque indicator scale means includes a substantially flat arcuate plate portion fixedly mounted to said bar member and including a plurality of torque related indicia along at least a portion of an outer periphery thereof, said torque-related indicia including a zero point index disposed on said torque indicator scale means in such a manner that a line passing through the zero point index extends through a line created by a contact between said substantially flat surfaces of said first and second rod means.

11. A measuring device according to claim 10, wherein said second rod means is mounted in said first barrel member with a frictional fit.

12. A measuring device according to claim 10, wherein means are provided on one of said second rod means or said first barrel member for providing frictional contact between said first barrel member and said second rod means.

13. A measuring device according to claim 10, wherein said second rod means is provided with an external threaded portion along at least a portion of an axial length thereof, and wherein said first barrel member includes an internal threaded portion along at least a portion of an axial length thereof engageable with the external threaded portion of said second rod means to permit an adjustable displacement of said second rod means relative to said first rod means.

14. A measuring device according to claim 13, wherein a grip means is provided at a free end of said second barrel member to facilitate an operation of said second barrel member.

15. A measuring device according to one of claims 2 or 3, wherein said support means includes a substantially flat axially extending bar member fixed to said first barrel member, said torque indicator scale means includes a sector-shaped plate member having a central opening therein, said torque indicator scale means including a plurality of torque-related indicia and a zero point index disposed along at least a portion of an outer periphery of said sector-shaped member in such a manner that a line passing through the zero point index extends through a line created by a contact between said substantially flat surfaces of said first and second rod means.

16. A measuring device according to claim 15, wherein said second rod means is mounted in said first barrel member with a frictional fit.

17. A measuring device according to claim 15, wherein means are provided on one of said second rod means or said first barrel member for providing frictional contact between said first barrel member and said second rod means.

18. A measuring device according to claim 15, wherein said second rod means is provided with an external threaded portion along at least a portion of an axial length thereof, and wherein said first barrel member includes an internal threaded portion along at least a portion of an axial length thereof, engageable with the external threaded portion of said second rod means to permit an adjustable displacement of said second rod means relative to said first rod means.

19. A measuring device according to claim 15, wherein a grip means is provided at a free end of said second barrel member for facilitating an operation of said second barrel member and permitting a fine adjustment of said releasable holding means.

20. A measuring device according to one of claims 2 or 3, wherein said torque indicator scale means is a protractor means having angular indicia along at least a portion thereof mounted on said support means in such a manner that a line passing through a midpoint of the angular indicia extends through a line created by a contact between substantially flat surfaces of said first and second rod means.

21. A measuring device according to claim 20, wherein said second rod means is mounted in said first barrel member with a frictional fit.

22. A measuring device according to claim 20, wherein means are provided on one of said second rod means or said first barrel member for providing frictional contact of said first barrel member and said second rod means.

23. A measuring device according to claim 20, wherein said second rod means is provided with an external threaded portion along at least a portion of an axial length thereof, and wherein said first barrel member includes an internal threaded portion along at least a portion of an axial length thereof engageable with the external threaded portion of said second rod means to permit an adjustable displacement of said second rod means relative to said first rod means.

* * * * *